United States Patent
Stief

(10) Patent No.: US 7,135,304 B2
(45) Date of Patent: Nov. 14, 2006

(54) TEST SYSTEM FOR THE DETERMINATION OF IN-VIVO ACTIVE HEMOSTASIS PROTEASES OR OF TRYPSIN OR SUBTILISIN IN BIOLOGICAL FLUIDS AND/OR THE USAGE THEREOF TO DETERMINE THE IN-VIVO ACTIVATION OF HEMOSTASIS OR TO DIAGNOSE A PANCREATITIS

(76) Inventor: Thomas W. Stief, Limesstrasse 15, 35415 Pohlheim (DE)

( * ) Notice: Subject to any disclaimer, the term of this patent is extended or adjusted under 35 U.S.C. 154(b) by 397 days.

(21) Appl. No.: 10/115,177

(22) Filed: Apr. 2, 2002

(65) Prior Publication Data
US 2003/0044876 A1  Mar. 6, 2003

(30) Foreign Application Priority Data
Apr. 3, 2001 (DE) ............................. 101 16 586

(51) Int. Cl.
*G01G 3/30* (2006.01)
*G01G 5/00* (2006.01)
*C12Q 1/68* (2006.01)

(52) U.S. Cl. ......................... 435/7.91; 435/212
(58) Field of Classification Search .................. 435/23, 435/212, 7.4, 7.91
See application file for complete search history.

(56) References Cited

U.S. PATENT DOCUMENTS

| | | | | |
|---|---|---|---|---|
| 4,275,153 A | * | 6/1981 | Gargiulo et al. | 435/13 |
| 4,801,534 A | * | 1/1989 | Mitchell et al. | 435/13 |
| 5,057,414 A | * | 10/1991 | Stief et al. | 435/13 |
| 5,955,576 A | | 9/1999 | Vlasuk et al. | |
| 6,187,594 B1 | | 2/2001 | Kraus et al. | |
| 6,451,610 B1 | * | 9/2002 | Gorman et al. | 436/69 |

FOREIGN PATENT DOCUMENTS

| | | |
|---|---|---|
| CA | 2 361 672 | 8/2000 |
| DE | 19549118 A1 * | 7/1997 |
| DE | 197 56 773 A1 | 6/1999 |
| DE | 199 04 674 A1 | 8/2000 |
| DE | 199 40 389 A1 | 3/2001 |

OTHER PUBLICATIONS

Ramjee, M. "The use of fluorogenic substrates to monitor thrombin gneration for the analysis of plasma and whole blood coagulation" Anal. Biochem. (2000) 277: 11-18.*
Prasa et al. "Determination of activated Factor IX in Factor IX concentrates with a chromagenic substrate" Thrombosis Res. (1998) 92: 99-102.*
Stief, T. "A direct approach in fibrinolysis diagnostic: mimicry of the leucocyte attack by oxidants," Thrombosis Res. (1989) 56(2): 213-220.*
Fassler et al. "Assay with chromogenic substrates of in vivo activated proteases" Haemostasis (1978) 7(2-3): 158-163.*
Stief et al. "Arginine inhibits hemostasis activation" Thrombosis Res. (Nov. 2001) 104: 265-274.*
Newell et al. "Hemolytic and antigenic measurements of complement" J. Lab. Clin. Med. (1982) 100: 437-444.*
Pfeifer et al. "Possible mechanism for in vitro complement activation in blood and plasma samples: Futhan/EDTA controls in vitro complement activation" Clin. Chem. (1999) 45(8): 1190-1199.*
Svendsen, L.G. et al., Newer Synthetic Peptide Substrates in Coagulation Testing: Some Practical Considerations for Automated Methods, Seminars in Thrombosis and Hemostasis, vol. 9, No. 4, 250-262 (1983).
Internet document, address: http://www.zentrallabor.uni-wuerzburg.de/commercial/dade.html, regarding Pathromtin SL, last update Mar. 9, 1999.
Stief, T.W. et al., A Simple Screening Assay for Certain Fibrinolysis Parameters (FIPA). Thrombosis Research 97 (2000) 231-237.

* cited by examiner

*Primary Examiner*—Jean C. Witz
*Assistant Examiner*—Susan Hanley
(74) *Attorney, Agent, or Firm*—Connolly Bove Lodge & Hutz LLP

(57) ABSTRACT

Test system for the determination of in-vivo active hemostasis proteases or of trypsin or subtilisin in biological fluids and the usage thereof to determine the in-vivo activation of hemostasis or to diagnose pancreatitis.

19 Claims, No Drawings

TEST SYSTEM FOR THE DETERMINATION OF IN-VIVO ACTIVE HEMOSTASIS PROTEASES OR OF TRYPSIN OR SUBTILISIN IN BIOLOGICAL FLUIDS AND/OR THE USAGE THEREOF TO DETERMINE THE IN-VIVO ACTIVATION OF HEMOSTASIS OR TO DIAGNOSE A PANCREATITIS

DESCRIPTION

Test system for the determination of in-vivo active hemostasis proteases or of trypsin or subtilisin in biological fluids and/or the usage thereof to determine the in-vivo activation of hemostasis or to diagnose a pancreatitis.

The present invention relates to a global procedure basing on peptide substrates for the determination of in-vivo active hemostasis proteases or of in-vivo active trypsin or of subtilisin in biological fluids, that particularly can be used to determine the in-vivo activation of hemostasis, particularly of the in-vivo activation of coagulation (GACA) and/or of the contact phase capacity (CPC) of biological fluids or to diagnose a pancreatitis and/or the severity grade of a pancreatitis.

Hemostasis is the system of generation and degradation of thrombi, i.e. hemostasis comprises blood coagulation and fibrinolysis. Normally, hemostasis enzymes occur in blood mainly in an inactive form, only a very small part of the respective hemostasis enzymes, that are mainly serine proteases, occur in vivo in an active form, i.e. there is in a very small degree of in vivo activation of hemostasis in the blood of the healthy organism. However, an enhanced in vivo activation of hemostasis is of great pathophysiologic importance in the pathogenesis of many diseases. Consequently, in a pathologically-increased in vivo activation of hemostasis (as in disseminated intravascular coagulation (DIC) or in thrombophilia) more hemostasis enzymes are found in activated form. The determination of this in vivo active hemostasis enzymes, i.e. the determination of the degree of in vivo activation of hemostasis, is of great medical importance for the diagnosis of diseases, that are linked to a changed in vivo activation of hemostasis.

While global tests for the determination of hemostasis exist since many years (e.g. prothrombin time (PT), activated partial thromboplastin time (APTT), thrombin time (TT), Kher et al. (1997) Haemostasis 27(5): 211–8), there is no simple global test, that measures the in vivo activation of hemostasis. The usual hemostasis tests such as APTT, PT, TT do not detect the in vivo activation of hemostasis; instead in these tests an activation of hemostais is induced in vitro, i.e. they measure the capacity of hemostasis and not the in vivo activation of hemostasis.

The up to date available tests for the activation of hemostasis only allow indirect conclusions respective the in vivo activation of hemostasis. With one group of these tests the activity of proenzymes of hemostasis (so called zymogens) is determined; these proenzymes, as a general rule, have to be converted into proteases, whereby only the in vitro activity of hemostasis enzymes is detected. In another group of these tests activation markers of hemostasis are determined with sumptuous protein additions, especially with antibodies or recombinant proteins. Both groups of tests are dependent on a multitude of influences that falsificate the in-vivo state of activation of hemostasis, resulting into false conclusions. Thus, even short time storage of samples may change, particularly amplify, the activity of hemostasis enzymes and a conclusion to the in-vivo state is practically impossible.

Tests according to the state of the art are tests on the hand for D-Dimer, Thrombin-Antithrombin-Komplex, Prothrombinfragment F1+2 or Factor XIIa or on the other hand for soluble fibrin or Factor VIIa (Stief (2000) Thromb Haemost 84: 1120–1; MacCallum et al. (2000) Thromb Haemost 83(3): 421–6; Bos et al. (1999) Thromb Haemost 81(3): 467–8; Cardigan et al. (1998) Blood Coagul Fibrinolysis 9(4): 323–32). These tests are very complicated, requiring the addition of specific proteins, that allow only an indirect conclusion respective the in vivo activity of the main enzymes of coagulation, i.e. Thrombin (Faktor IIa) and/or Factor Xa and/or other hemostasis proteases.

From DE-A-19904674 a method respective the determination of the concentration of thrombin inhibitors is known. The DE-A-19940389 describes selective inhibitors of urokinase-plasminogen activator. From DE-A-19756773 a new method and diagnostic agent for diagnosis of hemostasis.

In Thrombosis Research Vol. 97, No. 4, pp. 231–7 (2000) a Screening Assay for certain parameters of fibrinolysis is published.

None of these publications describes the presence of the main enzymes of coagulation (Thrombin and/or Factor Xa) in active form in vivo.

In the described systems of these publications hemostasis factors are detected, that are activated not until the detection procedure.

The known tests are very sumptuous, base on the addition and/or usage of expensive proteins (on the one hand antibodies or on the other hand pure hemostasis proteins) and only partially allow conclusions respective the in vivo activation of hemostasis. Thus, the performance of the described methods is not very economical and these methods do not measure the global state of in vivo activation of hemostasis, particularly not the global state of in vivo activation of hemostasis, particularly not the global state of in vivo activation of coagulation, but determine only a partial aspect of the activation of hemostasis.

Chromogenic and/or fluorogenic peptide-substrates are used according to the state of the art, to measure the activity of inhibitors of coagulation such as antithrombins and/or heparinoids in blood or to measure the hemostasis capacity (in vitro induced activation of hemostasis).

Up to now it was not known, that there is such a sufficient activity of hemostasis enzymes in vivo in blood, that enables a direct detection of the activity of these enzymes by means of chromogenic and/or fluorogenic substrates that a cleavable by hemostasis enzymes. The inventions is based on the realization, that a low grade activation of the hemostasis system is physiologic. However, this in-vivo activation is very small and up to now has not been used to determinde the grade of activation of hemostasis.

Besides the determination of the in-vivo activation of hemostasis of special interest is as a further application possibility the diagnosis of a septicemia and/or a pancreatitis and/or the grading of the severity of a pancreatitis. Particularly there is no clinical-chemical test available for the grading of the severity of a pancreatitis (state of the art: Kylänpää-Bäck ML et al. JOP. Journal of the Pancreas (Online) 2002; 3: 34–48).

In pancreatitis there is the serine protease trypsin in the blood of the patients. By the determination of in-vivo active trypsin it is possible, to get informations on the grade of severity of the pancreatitis.

With the present invention for the first time a test system is presented, that determines in-vivo activity of hemostasis proteases or of trypsin or subtilisin, particularly that of an in-vivo activation of hemostasis or in-vivo active trypsin or subtilisin, both in normal samples and in patient samples. Of particular importance is the detection in time of hypercoagulabile conditions, because these are or might become life-threatening. The test system according to the invention allows for the first time, to diagnose thrombophilia and disseminated intravascular coagulation (consumption coagulopathie) at an early stage.

An object of the present invention is, to provide a procedure for the determination of in-vivo active hemostasis proteases, preferably of serin proteases or of in-vivo active trypsin or subtilisin, particularly the in-vivo activation of hemostasis of biological fluids, or in-vivo active trypsin in biological fluids, particularly of blood or blood plasma. With this information the degree of in-vivo activation of hemostasis or of the degree of severity of pancreatitis or septicemia can be assessed.

Surprisingly it was found now, that the in vivo activation of hemostasis can be determined by incubation of biological fluids with chromogenic or fluorogenic substrates for in-vivo active serine proteases.

Subject of the present invention is therefore a method to determine the in-vivo activity of hemostasis proteases or of trypsin and/or of subtilisin in biologial fluids, preferably to determine the in-vivo activity of serine proteases in biological fluids, characterized thereby, that the biological fluid after withdrawel is incubated with at least one chromogenic or fluorogenic substrate, preferably a peptide substrate, for at least one hemostasis protease or of trypsin and/or of subtilisin, particularly for at least one hemostasis enzyme or for trypsin.

Subject of the present invention is furthermore a test system for the determination of in-vivo active hemostasis proteases or of trypsin and/or of subtilisin in biological fluids, characterized thereby, that the test system comprises a chromogenic or fluorogenic substrate for at least one hemostasis protease or for trypsin and/or for subtilisin, particularly for at least one hemostasis enzyme or for trypsin.

Further subject of the invention is the usage of this test system, particularly the usage of chromogenic or fluorogenic substrates for at least one hemostasis enzyme to determine the in vivo activation of hemostasis in biological fluids or the usage of chromogenic or fluorogenic substrates for trypsin or subtilisin to determine in-vivo activation of in-vivo active trypsin or subtilisin in biological fluids.

Subject of the present invention is further a diagnostic agent for the determination of the in vivo activation of hemostasis or for the determination of in-vivo active trypsin and/or subtilisin in biological fluids, containing at least one chromogenic or fluorogenic substrate for at least one hemostasis enzyme and/or containing at least one chromogenic or fluorogenic substrate for trypsin and/or subtilisin and optionally further additives.

Biological fluids in the sense of the present invention are generally spoken body fluids that are derived from body cells, such as cell cultures, that are e.g. derived from endothelial cells, compartment fluids, and preferably blood and/or plasma, particularly EDTA-blood, EDTA-plasma, EDTA/arginine-blood or EDTA/arginine-plasma.

Sample material for the determination of the activation of hemostasis according to the state of the art is citrated blood and/or citrated plasma. Samples supplemented with other anticoagulants such as EDTA-blood and/or EDTA-plasma or EDTA/arginine-blood and/or EDTA/arginine-plasma up to now has not been used for this purpose.

The procedure according to the invention can be performed with citrated blood or citrated plasma, respectively, but also with blood or plasma, that are supplemented with other anticoagulants, such as heparin, singlet oxygen generators such as Chloramines, particularly ChloramineT® (N-chloro-toluolsulfonamide), EDTA, EGTA, arginine and/ or guanidine.

Surprisingly it occured, that EDTA-blood and EDTA-plasma, or EDTA/arginine-blood and EDTA/arginine-plasma, respectively, are especially suitable, to determine the in vivo activation of hemostasis, or in-vivo active trypsin and/or subtilisin, respectively. Instead of EDTA or arginine also guanidine or chloramine T® (N-chloro-p-toluene-sulfonamide), respectively, or a combination of these substances with or without EDTA can be used.

EDTA and/or arginine and/or guanidine or chloramine T® are preferably added already at the time of blood sampling.

Subject of the present invention is furthermore a method to diagnose the in vivo activation of hemostasis or in-vivo active trypsin and/or subtilisin of a biological fluid, whereby as biological fluid EDTA-blood or EDTA-plasma, arginine-blood or arginine-plasma or EDTA/arginine-blood or EDTA/ arginine-plasma is used.

The procedure according to the invention to determine the in vivo activation of hemostasis or of in-vivo active trypsin and/or subtilisin is characterized thereby, that it is a very simple, practicable, precise and economical procedure to determine the in vivo activation of hemostasis or of in-vivo active trypsin and/or subtilisin, that allows the investigation of blood samples of a great quantitiy of samples.

With the procedure according to the invention the CV-values (coefficients of variations) are without problems less than 5%, whereas the above described known tests for active enzymes of hemostasis CV-values result of more than 10%.

The values of hemostasis activation or of active trypsin and/or subtilisin, respectively, that can be determined according to the invention, are particularly the uncorrected activation of coagulation (uGACA) and the corrected activation of coagulation (GACA), whereby GACA stands for Global Assay of in vivo Coagulation Activation.

Basing on the uGACA-value, particularly the coagulation activation (GACA), corrected by the contact phase capacity (CPC), can be determined.

According to the invention the procedure to determine the GACA-value is performed in such a way, that the biological fluid after withdrawel is mixed with a buffer, if appropriate an anticoagulant and further additives, a chromogenic or fluorogenic substrate, and thereafter this mixture in incubated.

It has resulted, that the procedure according to the invention in a general rule should be performed at final substrate concentrations $\leq 2$ mmol/l (respectively $\leq 2$ mM) and/or at substrate amounts $\leq 3$ nmoles/pl sample). The usage of higher concentrations and/or amounts of substrate can result into an indesired activation of proenzymes of hemostasis. The desired sensitivity of the test determines the lower limit of the substrate concentration. The necessary concentration and/or amount can be determined by the expert, using the schemes of the examples.

Preferably final substrate concentrations of 0.05 to 1 mM and/or substrate amounts of $\leq 1.5$ nmoles/ul sample, particularly 0.05 to 0.8 mM and especially prefered 0.5 to 0.6 mM are used.

In the range inferior to 1 mM, particularly 0.5–0.6 mM, the determination of uGACA aproximately corresponds to the final GACA-value, whereas unspecific proteases are active principally at higher substrate concentrations. Only at substrate concentrations >1 mM it is recommendable as a rule to correct the obtained uGACA by the CPC.

The increase in absorbance, fluorescence and/or extinction during the incubation time of the sample can be determined with a spectrometer and/or spectroscope. Instead of this base level and final level of the absorbance, fluorescence and/or extinction can be determined.

The determination of the flureszence, extinction and/or absorption is preferably performed at a defined for the chromophore of the chromogenic or fluorogenic substrate characteristic wave length, particularly at a wave length, at which results after cleavage of the substrate by the coagulation enzyme a significant, i.e. spectroscopically and/or spectrometrically detectable change of the fluorescence, extinction and/oer absorbance. These values are absolute ones for the activation of coagulation (uGACA).

The incubation period according to the invention is between 0.5 and 180 minutes at a temperature between 30 und 50° C., particularly perfered at a temperature between 37 und 45° C., especially prefered at 37° C. or between 40 and 45° C. Using incubation at 37° C., the incubation period is 0.5 to 120 minutes, using inncubation between 42 und 45° C., the incubation period is preferably 0.5 to 60 minutes.

To determine the procentual GACA-value the measured absorbance/fluorescence-values of the samples are compared with a 100% set value of the normal polulation. Therefore, the values of the activation of coagulation of a standard or samples of healthy indiviuels are determined and the mean value (=100%) is calculated. The result obtained for the patient sample is expressed in percent of the 100% normal standard (as in standard human plasma and/or control plasma N®, DadeBehring).

Since especially also the proenzymes of the contact phase of hemostasis cleave the used chromogenic substrates amidolytically, the obtained uncorrected GACA-value if appropriate is corrected by the contact phase capacity (CPC) of the sample. This is preferably determined in a 1-step oder 2-step procedure (see examples). To determine the 1-step-CPC the biological fluid is mixed with a buffer, if appropriate an anticoagulant and further additives, a chromogenic or fluorogenic substrate and a contact phase activator. Thereafter, the mixture is incubated, preferably at a temperature between 15 und 37° C., preferably inferior to 30 minutes, especially prefered between 0.1 and 10 minutes, particularly for 0.2 to 2 minutes (at 37° C.).

Determination of absorbance, fluorescence and/or extinction occurs here such as described for the procedure to determine the uGACA-value. Values for the contact phase capacity of healthy probands are measured, thereafter a mean value (100%) is calculated. The obtained value for the patient samples is expressed in percent of the 100% value of the healthy probands=100% normal standard (such as in standard human plasma and/or control plasma N®).

As contact phase activator according to the invention preferably kaolin, ellagic acid, or particularly $SiO_2$ is used.

Kaolin is preferably used at a test concentration between 0.1 and 4 g/l, especially prefered at a test concentration between 0.2 and 2 g/l, particularly at 0.8 g/l. Ellagic acid is preferably used at a concentration between 0.01 and 0.3 g/l, particularly prefered between 0.02 and 0.2 g/l, especially at 0.075 g/l. As $SiO_2$ reagent Pathromtin SL® (Dade Behring, Marburg, Germany) can be used, 1:2 to 1:16 fold in the assay diluted, especially prefered 1:3 to 1:8 fold in the assay diluted, particularly 1:4 fold diluted.

Surprisingly it has been found, that the additional supplementation of the contact activator can be omitted, if for the determination of the CPC a chromogenic substrate is used, whose end group serves as a contact activator. Examples for such substrates are methoxysulfonated oder acetylated substrates for hemostasis enzymes, such as $CH_3SO_2$-D-CHG-Gly-Arg-pNA.AcOH, Pefachrome®FIXa (Pefa-3107; Pentapharm, Basel, Switzerland).

The additional supplementation of a contact phase activator can be omitted, if as chromogenic substrate for the determination of the CPC a substrate is used, whose end group acts as an activator of the contact phase (such as e.g. $CH_3SO_2$-D-CHG-Gly-Arg-pNA.AcOH, Pefachrome®FIXa (Pefa-3107); Pentapharm, Basel, Schweiz).

The determination of the GACA-value and of the CPC proceeds preferably according to the invention by monitoring the absorbance, fluorescence and/or extinction at a certain—for the chromophore and/or fluorophore of the chromogenic and/or fluorogenic substrate characteristic wave length.

Thus, the procedure includes according to the invention particularly prefered the following steps of procedure:

a) determination of the activation of hemostasis for samples of patients by addition of a chromogenic and/or fluorogenic substrate to each sample or to a standard sample, respectively; spectroscopic and/or spectrometric determination of the change in absorbance, fluorescence and/or extinction of the sample at at least one defined wave length, calculation of the uGACA-value by comparison of the patient samples with a known standard sample (plasma or pure enzyme (e.g. Factor Xa or Thrombin)) and expression in percent of the mean value of healthy probands.

b) determination of the CPC in analogue manner as the determination of the uGACA, with the exception that additionly a contact phase activator is added to the samples, and c) determination of the GACA-value, corrected for the CPC, by subtraction of CPC from UGACA and addition of 100%.

In the range inferior to 1 mM, particularly 0.05–0.8 mM, especially preferred 0.5–0.6 mM, the determination of UGACA aproximately corresponds to the final GACA-value, whereas unspecific proteases as a rule are active principally at higher substrate concentrations. Only at substrate concentrations $\geq 1$ mM it is recommendable as a rule to correct the obtained uGACA by the CPC.

Preferably the substrate used is dissolved in EDTA and/or arginine, so that a final test concentration of EDTA of at least 2.1 g/l and one of arginine (of a basic pH-value) of at least 250 mmol/l is resulting.

The sample is here a biological fluid, the defined wave length is a characteristic wave length of the chromophore of a chromogenic or fluorogenic substrate. The biological fluid is according to the invention blood or blood plasma, particularly prefered EDTA-blood or EDTA-plasma, arginine-blood or arginine-plasma or EDTA/arginine-blood or EDTA/arginine-plasma.

To perform the test according to the invention the biological fluid is mixed particularly with a buffer, particularly phosphate buffered saline (PBS), $HCO_3^-$, arginine, or Tris at pH 7–11, preferably pH 7–9, especially pH 7.4 for PBS or pH 8.7 for arginine. Together with the buffer also other anticoagulants can be used according to the invention, to prevent the in vitro occuring (i.e. artificial) hemostasis activation in the biological fluid during the GACA-test incubation, such as e.g. Ethylene Diamine Tetraacetic Acid (EDTA), Ethylene Glycol-bis(β-aminoethyl Ether)N,N,N',N'-Tetraacetic Acid (EGTA), arginine, guanidine saltsor singlet oxygen generators, particularly of the type of the chloramines.

In contrast to the usage of EDTA, where the addition of further anticoagulants is not absolutely necessary, is the relatively-mild calcium complexation by citrate as a rule not sufficient, to prevent an additional in vitro hemostasis activation of the blood plasma in the assay, so that here according to the invention further anticoagulants are added. Thus, according to the invention e.g. peferably EDTA, in a concentration of 0.8 to 2.4 mg/ml, particularly 1.6 mg/ml (4,4 mmol/l blood correspond to about 8 mmol/l plasma) is used to stabilize the blood sample. The investigation of citrated blood requires the addition of a further anticoagulant in the assay: using citrated plasma as a further anticoagulant EDTA might be used, prefered in test concentrations between 2–20 mmol/l, particularly 5–10 mmol/l, and/or arginine, prefered at a test concentration between 50–500 mmol/l, particularly 80–300 mmol/l, particularly prefered 250 mmol/l.

The chromogenic and/or fluorogenic substrates for proteases, particularly for hemostasis enzymes or trypsin and/or subtilisin are according to the invention peptides with an amino acid sequence, that are cleaved amidolytically by hemostasis enzymes or trypsin and/or subtilisin, respectively, particularly prefered by Factor Xa and/or thrombin and/or other hemostasis serine proteases; the substrates possess a chromophore, whereby it results after the amidolytic cleavage of the substrates by the hemostasis enzyme or by trypsin and/or subtilisin, respectively, a change in absorbance- and/or in the fluorescence spectrum of the chromophore, that can be detected spectroskopically or spectrometrically.

Preverably these substrates comprise 2 to 10, particularly prefered 2, 3, 4 or 5 amino acids. The amino acids might also be non-proteinogenic or naturally not occuring organic compounds. Furthermore, the substrate might be modified, e.g. by ligation of at least one protection group, at least one marked group and/or at least one organic compound. The chromogenic and/or fluorogenic group is particularly covalently ligated to the carboxyterminal amino acid of the substrate.

As chromogenic substrates are suitable according to the invention e.g. substrates for hemostasis enzymes, that possess para-nitroaniline (pNA) as chromophore, particularly thrombin and/or Factor Xa- substrates, e.g. the following substrates:

HD-CHG-Ala-Arg-pNA.2AcOH, Pefachrome®TH (Pefa-5114), Pentapharm, Basel, Schweiz;

HD-CHA-Ala-Arg-pNA, Instrumentation Laboratory (IL), Lexincton, USA;

HD-Ile-Phe-Pip-Arg-pNA HCl (HD-Phenylalanyl-L-pipecolyl-L-arginine-para nitroanilide; S-2238®), Chromogenix, Mölndal, Sweden;

HD-HHT-Gly-Arg-pNA; HHT=Cyclohexyltyrosin; CHG=Cyclohexylglycin; CHA=β-Cyclohexylalanin; pNA=para-Nitroanilide; Pefachrome®FXIIa (Pefa-5963), Pentapharm N-α-Z-D-Arg-Gly-Arg-pNA.2HCl (S-2765®), Chromogenix, Mölndal, Sweden;

Bz-Ile-Glu(γ-OR)Gly-Arg-pNA-HCl (S-2222®), Chromogenix, Mölndal, Sweden;

HD-Ile-Pro-Arg-pNA.HCl (S-2288®), Chromogenix, Mölndal, Sweden;

-CO-Ile-Glu-(γ-OR)-Gly-Arg-pNA (FXa, Trypsin; S-2222®), Chromogenix

HD-Val-Leu-Arg-pNA (Kallikrein; S-2266®), Chromogenix

D-Pro-Phe-Arg-pNA (Kallikrein; S-2302®), Chromogenix.

Examples for subtilisin substrates, particularly for the diagnosis of a septicemia, are Z-Gly-Gly-Leu-pNA, Z-Ala-Ala-Leu-pNA, Suc-Ala-Ala-Ala-pNA, Suc-Ala-Ala-Phe-pNA, and particularly Suc-Phe-Ala-Ala-Phe-pNA (Bachem, Heidelberg, Germany. Trypsin as a broad spectrum-serine protease particularly cleaves chromogenic and/or fluorogenic substrates with end positioned basic aminoacid-(particularly arginine or lysine)-chromophore group.

For the determination of the CPC additional substrates can be used, that are cleaved particularly by proenzymes of the contact phase. These are e.g.

$CH_3SO_2$-D-CHA-Abu-Arg-pNA

Pefa IXa ($CH_3SO_2$-D-CHG-Gly-Arg-pNA)

Pefa VIIa (CH3SO2-D-CHA-But-Arg-pNA)

Pefa Xa ($CH_3OCO$-D-CHA-Gly-Arg-pNA)

These substrates are characterized thereby, that they are cleaved by the contact phase enzymes even in presence of arginine (even in concentrations >100 mM).

According to the invention the procedure is performed e.g., that for the determination of the UGACA 100 μl EDTA-plasma is incubated with 50 μl 3 mmol/l peptide substrate for 0.25–2 h at 370 or for half the time at 40–45° C. The increase in extinction at 405 nm is determined. The result [A] is compared with a known standard (e.g. a 100% normal standard human plasma or pure enzyme (6 mIU/ml thrombin or 45 pkat/ml FXa)) and expressed in %. The normal uGACA-value is 100±50% (mean±2 standard deviations of a normal collective).

For determination of the contact phase capacity 100 μl sample are then incubated with 50 μl chromogenic substrate and 50 μl of a contact activator (e.g. kaolin 2.5 g/l (Pathromtin®), DadeBehring, Marburg, Germany), ellagic acid 0.3 g/l (Neothromtin®, DadeBehring) or $SiO_2$ (Pathromtin SL®, DadeBehring) for 4 min at room temperature (RT). Also here the resutl [B] is compared with a 100% normal standard human plasma and expressed in percent. The correction formula for calculation of the specific GACA-value is consequently:

$$GACA = A - B + 100\%.$$

In a particularly prefered version of the procedure according to the invention a final substrate concentration of less than 1 mmol/l is used; at substrate concentrations inferior to 0.8 mmol/l as a rule the uGACA-value is aproximately the GACA-value. The determination of the CPC can thus be omitted. Therefore, a GACA-approach of particular importance is the incubation of 100 μl sample (e.g. plasma) with 50 μl 1.7 mmol/l peptide substrate (such as a thrombin substrate, especially CHG-Ala-Arg-pNA) in 750 mmol/l arginine, pH 8.7, 6.4 g/l EDTA.

The normal GACA (and CPC)-value is 100±50% (mean±2 standard deviations).

The invention shall be explained by the following examples; the intention of these examples is not to limit the idea of the invention:

EXAMPLE 1

Example GACA and Example CPC

The GACA is performed here as follows: 100 μl sample (preferably EDTA-Plasma) of a) n=10 normal donors and b) n=35 patients are incubated with 50 μl 3 mmol/l chromogenic substrate HD-CHG-Ala-Arg-pNA in phosphate buffered saline (PBS) pH 7.4, preferably containing 15–30 mmol/l EDTA, particularly 20 mmol/l EDTA, in a mikrotiterplate and the basal extinction at 405 nm is determined by a mikrotiterplate photometer (Milenia, DPC, Los Angeles, USA). After an incubation of 90 min at 37° C. the extinction at 405 nm is again determined and the difference to the basal extinction is calculated.

Result: The normal range of GACA (mean value ±2 standard deviations (a), calculated from normal donors) is 100±50%, i.e. the normal uGACA-Activity is 254±116 mA/90 min (37° C.). The patients had a mean uGACA-value of 471±154 mA/90 min (37° C.). This uGACA-value was calculated in % normal plasma [A], the value determined was thus 471/254=185%.

Additionally, the contact phase capacity (CPC) of the plasmas used was determined, to correct the obtained uGACA-value, i.e. to get a GACA-value that is independent of the contact phase. Herefore 100 µl sample was incubated with 50 µl 3 mmol/l HD-CHG-Ala-Arg-pNA in PBS, pH 7.4, 20 mmol/l EDTA and 50 µl Pathromtin SL® ($SiO_2$; Dade Behring) for 5 min at room temperature (RT) in a mikrotiterplate. It resulted a normal CPC of 1319±439 mA (=100±33%)/5 min (RT) (the patients had a CPC of 1339±442 mA/5 min (RT)). The CPC of the individuel patients was calculated in in % activity compared with a 100% standard normal plasma. The activity obtained by this procedure [B=CPC] is subtracted from the activity [A=uGACA] and 100% is added, resulting in GACA, corrected by contact phase:

GACA=$A-B$+100%

EXAMPLE 2

Optimization of the Test Concentration of Contact Phase Activator in the CPC

To optimize the contact phase activator in the CPC 100 µl
a) Neothromtin® (0.6 g/l ellagic acid (3 ml vial Dade Behring in 1.5 ml $H_2O$)
b) Pathromtin® (5 g/l Kaolin, Dade Behring)
c) Pathromtin SL® ($SiO_2$, Dade Behring)

in 1:1, 1:2, 1:4, 1:8, 1:16, 1:32, 1:64, 1:128 dilution with $H_2O$ or for control 100 µl $H_2O$ were incubated with 100 µl 1.5 mmol/l HD-CHG-Ala-Arg-pNA in PBS and with 100 µl normal plasma (citrated) for 4 min (RT). The increase in extinction (405 nm)/4 min was determined.

Result: Optimal activity of protease occurs at a test concentration of 0.8 g/l (0.2–2 g/l) Kaolin (delta A=2138 mA/4 min; e.g. Pathromtin Dade Behring Marburg), 0.05 g/l (0.02–0.2 g/l) ellagic acid (delta A=1443 mA/4 min) and 17% (8.5–50%) test concentration of $SiO_2$ compared to that in Pathromtin SL® (delta A=1375 mA/4 min).

EXAMPLES 3–19

In the following Examples a Global Assay of Coagulation Activation=GACA is Described.

Test-scheme GACA:

| | |
|---|---|
| 100 µl | Sample |
| 50 µl | 1.7 mM HD-CHG-Ala-Arg-pNA, 6.4 g/l EDTA, 750 mM Arginine, pH 8.7 Δ A 405 nm/t (37° C.) |

-continued

Testvolumina changeable in the same proportion (i.e. e.g. 200 µl Sample + 100 µl Substrate)
Sample = Plasma or Blood, especially Arginine-stabilized EDTA-Plasma
(2.6 ml EDTA-Blood + 300 µl 1.5 M Arginine)
EDTA-Plasma (not older than 2 h)
Citrat-Plasma (not older than 2 h)
where appropriate Heparin-Plasma
Contact Phase Capacity
Test-scheme 1-step-CPC:

| | |
|---|---|
| 100 µl | Sample |
| 50 µl | 1.7 mM HD-CHG-Ala-Arg-pNA, 6.4 g/l EDTA, pH 7.4 |
| 50 µl | Pathromtin SL ® Δ A 405 nm/30 s (37° C.) |

Test-scheme 2-step-CPC:

| | |
|---|---|
| 100 µl | Probe |
| 50 µl | Pathromtin SL ® 60 s (37° C.) |
| 50 µl | 1.7 mM HD-CHG-Ala-Arg-pNA 6.4 g/l EDTA, 750 mM Arginine, pH 8.7 Δ A 405 nm/min (37° C.) |

EXAMPLE 3

Optimization of the Concentration of Substrate

100 µl normal EDTA-Plasma (pooled normal plasma) with 250 mM arginine, pH 8.7, or normal EDTA-Plasma, supplemented with 120 IU/ml bovine thrombin (F IIa) and 30 min thereafter with 250 mM arginine, pH 8.7 (=pathoplasma), and enzyme controls with 2 mIU/ml or 120 mIU/ml bovine thrombin in 500 mM arginine, 2% Haemaccel®, pH 8.7, were incubated with 50 µl HD-CHG-Ala-Arg-pNA of increasing concentrations (0–6.67 mM final test-concentration) in aqua dest. for 2 h at 37° C. Before and after the incubation the extinction at 405 nm was determined.

Result: Table 1 shows the enzyme-activities (enz.-act.) of normal plasma and of pathoplasma in dependance of the final concentration of the chromogenic substrate HD-CHG-Ala-Arg-pNA.

TABLE 1

Optimization of the concentration of substrate

| Final Conc. of Substrate [mM] | Enz.-act. Normal Plasma [mA/2 h] | Enz.-act. Pathoplasma [mA/2 h] |
|---|---|---|
| 0 | 0 | 0 |
| 0.095 | 43 | 168 |
| 0.19 | 78 | 276 |
| 0.28 | 116 | 412 |
| 0.37 | 149 | 506 |
| 0.41 | 165 | 538 |
| 0.45 | 189 | 580 |
| 0.5 | 210 | 616 |
| 0.55 | 233 | 669 |
| 0.61 | 269 | 707 |
| 0.68 | 304 | 767 |
| 0.76 | 352 | 821 |
| 0.84 | 390 | 868 |

TABLE 1-continued

Optimization of the concentration of substrate

| Final Conc. of Substrate [mM] | Enz.-act. Normal Plasma [mA/2 h] | Enz.-act. Pathoplasma [mA/2 h] |
|---|---|---|
| 0.94 | 401 | 914 |
| 1.04 | 428 | 928 |
| 1.19 | 518 | 999 |
| 1.29 | 623 | 1130 |
| 1.39 | 667 | 1217 |
| 1.58 | 744 | 1268 |
| 1.76 | 839 | 1379 |
| 1.95 | 950 | 1502 |
| 2.18 | 1024 | 1563 |
| 2.38 | 1159 | 1668 |
| 2.67 | 1295 | 1812 |
| 2.97 | 1420 | 1885 |
| 3.33 | 1552 | 2032 |
| 6.67 | >3000 | >3000 |

The ratio of the extinctions of pathoplasma and normal plasma aproximates the value of 1 at final substrate concentrations >1.5 mM. The higher this value the more specific is the assay for pathologic activation of hemostasis., here imitated by addition of 120 mIU/ml bovine thrombin. This ratio reaches maximal values at final substrate concentrations $\leq 1$ mM. However, the maximal change in extinction decreases at low substrate concentrations, especially at substrate concentrations below 0.3 mM, i.e. substrate exhaustion occurs. Therefore the final substrate concentration in the GACA should be between 0.3 mM and 1.0 mM, preferentially between 0.5 mM and 0.8 mM, particularly at 0.56 mM. At this final substrate concentration the assay is very specific for activation of hemostasis, and consequently the determination of CPC (approach B) can be neglected where appropriate. Thus, the GACA-value corresponds to the uGACA-value at a final substrate concentration of up to 0.8 mM, i.e. GACA=approach A (without correction by approach B). After addition of thrombin to EDTA-plasma 90% of thrombin is inactivated, in the GACA only 10% of the added enzyme activity can be detected.

EXAMPLE 4

Determination of the Km-value for Thrombin in Plasma

1. Normal EDTA-plasma with 250 mM arginine, pH 8.7, and 2. normal EDTA-plasma, supplemented with 120 mIU/ml bovine thrombin and 30 min thereafter with 250 mM arginine, pH 8.7, were incubated with 50 µl HD-CHG-Ala-Arg-pNA (0–6.67 mM final) in aqua dest. Delta A/3 h (37° C.) was measured and the value of 1. was subtracted from the value of 2. The resulting difference corresponds to the activity of thrombin in plasma after addition of 120 mIU/ml thrombin (F IIa). Result: the maximal enzyme velocity is 800 mA/3 h, the substrate concentration at halfmaximal velocity ($K_m$-value) is 0.3 mM.

EXAMPLE 5

Exhaustion of Substrate

To determine the maximal (max.) changes of extinction and the exhaustion of substrate, the incubation times of example 3 were increased to 24 h. Delta A >2000 mA result at final substrate concentrations (conc.) $\geq 0.7$ mM. Linearity between incubation time and change of extinction is guaranted at extinction changes up to 1000 mA at a final substrate concentration of 0.6 mM. Subtrate concentrations <0.4 mM result in maximal changes of extinction of <1000 mA with a linearity between incubation time and change in extinction of <500 mA (Table 2).

TABLE 2

Exhaustion of Substrate

| Final Conc. of Substrate [mM] | Max. Increase of Extinction [mA] |
|---|---|
| 0 | 0 |
| 0.095 | 234 |
| 0.19 | 468 |
| 0.28 | 702 |
| 0.37 | 935 |
| 0.41 | 1219 |
| 0.45 | 1435 |
| 0.5 | 1553 |
| 0.55 | 1720 |
| 0.61 | 1853 |
| 0.68 | 2048 |
| 0.76 | 2123 |
| 0.84 | 2184 |
| 0.94 | 2277 |
| 1.04 | 2348 |
| 1.19 | 2523 |
| 1.29 | 2697 |
| 1.39 | 2707 |
| 1.58 | 2714 |
| 1.76 | 2837 |
| 1.95 | 2913 |
| 2.18 | 3050 |
| 2.38 | 3043 |
| 2.67 | 3271 |
| 2.97 | 2933 |
| 3.33 | 2827 |
| 6.67 | 2748 |

EXAMPLE 6

Optimization of Substrate Concentration in Arginine/EDTA-Addition

Conditions of incubation as in example 3; but here the plasma STA Preciclot I® (Roche) was used, supplemented with 3.2 g/l EDTA. As pathoplasma STA Preciclot I® plasma with EDTA was used, that was supplemented with 120 mIU/ml thrombin and with 250 mM arginine. The chromogenic substrate HD-CHG-Ala-Arg-pNA was in 750 mM arginine, 6.4 g/l EDTA, pH 8.7. Thus, the test-concentration of arginin was 417 mM. The incubation time was 3 h (37° C.).

Result: see table 3. Also here results an optimal final substrate concentration of up to 0.8 mM, preferably of 0.05 to 0.7 mM, particularly 0.5 to 0.6 mM at this GACA-approach (100 µl sample+50 µl substrate).

TABLE 3

Optimization of the concentration of substrate, using 750 mM arginine-reagent

| Final Conc. of Substrate [mM] | Enz.-act. Normal Plasma [mA/3 h] | Enz.-act. Pathoplasma [mA/3 h] |
|---|---|---|
| 0 | 0 | 0 |
| 0.1 | 33 | 112 |
| 0.14 | 40 | 134 |

TABLE 3-continued

Optimization of the concentration of substrate, using 750 mM arginine-reagent

| Final Conc. of Substrate [mM] | Enz.-act. Normal Plasma [mA/3 h] | Enz.-act. Pathoplasma [mA/3 h] |
|---|---|---|
| 0.19 | 64 | 213 |
| 0.25 | 74 | 244 |
| 0.33 | 94 | 302 |
| 0.44 | 126 | 391 |
| 0.59 | 160 | 481 |
| 0.79 | 205 | 619 |
| 1.05 | 284 | 731 |
| 1.4 | 372 | 902 |
| 1.87 | 515 | 1094 |
| 2.15 | 721 | 1260 |
| 3.33 | 822 | 1477 |

EXAMPLE 7

Standardization of GACA with a Pure Enzyme-Reagent

The GACA was performed with 100 µl pure bovine thrombin (0–18 mIU/ml; DadeBehring), pure bovine Factor Xa (0–150 pkat/ml) or a Factor-Eight-Inhibitor-Bypassing-Activity-concentrate (0–2.6 units/ml; FEIBA®, Immuno, Wien) in 500 mM arginine, 2% Hamaccel, 0.1% Triton X 100® (substrate here =HD-CHG-Ala-Arg-pNA. Additional samples were Control Plasma N® (CPN, DadeBehring) oder CPN supplemented with FEIBA (0–2.6 Einheiten/ml). Die incubation was varied from 0 to 4 h. The respective change in extinction was measured. Result: There appears a linear relationship between the thrombin- or factor Xa- concentration used and the resulting change in extinction. Extinktionsänderung, and between incubation time and change in extinction. 6 mIU/ml IIa oder 45 pkat/ml Xa result in a change in extinction, that corresponds to that of normal plasma (100% GACA). Thus, the GACA can be calibrated and standardized with pure thrombin- or factor Xa- reagent. CPN with 2.6 units/ml FEIBA has a GACA-value of aprox. 200%, i.e. this addition of FEIBA to CPN increases the GACA-value from 100% to another 100%. Pure FEIBA in buffer shows a 10 fold higher activity, i.e. in CPN 90% of the added FEIBA is inactivated.

EXAMPLE 8

Optimum of Reaction Temperature and of pH in the GACA

The GACA was performed with STA Preciclot I®-plasma (100% GACA-activity; Roche), containing additionally 3.2 mg/ml EDTA, with STA Preciclot I®-plasma, containing additionally 3.2 mg/ml EDTA and 60 mIU/ml bovine thrombin, with a pool of citrated plasma of patients, containing additionally 3.2 mg/ml EDTA, with this pool of citrated plasma, containing additionally 3.2 mg/ml EDTA and 60 ml U/ml thrombin and with a pure thrombin-reagent, containing 6 mIU/ml thrombin in 500 mM arginine, 2% Haemaccel®, 0.1% Triton X 100®, pH 8.7. For this purpose 100 µl sample were incubated with 50 µl 1.7 mM HD-CHG-Ala-Arg-pNA in 750 mM arginine, 6.4 g/l EDTA, pH 7.5 to pH 11 each for 30 min. In other approaches both sample- and reagent-volume were doubled. The temperature of incubation was 37° C. to 52° C. Result: a maximum of activity appeared at 40° C. to 43° C. with approximately the twofold increase in extinction compared with 37° C. Therefore, a higher increase in absorbance results by using a reaction-temperature between 37° C. and 49° C., particularly between 40° C. and 43° C. The pH optimum is at pH 8 to pH 9. A twofold sample- or reagent-volume results into a twofold increase in extinction due to the increase in the layer thickness of the test cuvette.

EXAMPLE 9

No Correlation Between Prothrombin Time, APTT, Fibrinogen and GACA

For n=46 patient plasmas and CPN (both in GACA and in CPC 100% activity) the prothrombin time (PT), APTT, fibrinogen (fbgen) was determined and the GACA (100 µl sample or 100 µl 6 mIU/ml thrombin +50 µl 1.7 mM HD-CHG-Ala-Arg-pNA in 6.4 g/l EDTA, 750 mM arginine, pH 8.7; determination of delta A/t (here t=2 h and temperature =37° C.)) was performed. The results of the classical coagulation tests ste PT, APTT and fibrinogen were correlated with the GACA-value. Result: the coefficients of correlation (r) were: r (PT/GACA)=0.062; r (APTT/GACA) =0.030; r (Fbgen/GACA)=0.337. Thus, the GACA as an assay for in-vivo-activation of coagulation does not correlate with the classical tests of coagulation (PT, APTT, fbgen).

EXAMPLE 10

Stability of Samples

Control Plasma N (DadeBehring), supplemented with 3.2 mg/ml EDTA and CPN, supplemented with 3.2 mg/ml EDTA and 120 mIU/ml bovine thrombin were incubated for 0–17 h at room temperature (RT) or frozen at −80° C. eingefroren and thawed at 37° C. and then the GACA was performed (100 µl sample +50 µl 1.7 mM HD-CHG-Ala-Arg-pNA in 6.4 g/l EDTA, 750 mM arginine, pH 8.7). Result: Freezing/Thawing ati −80° C./37° C. does not change the GACA-value. The stability of samples that are not stabilitzed by arginine is approx. 2 h. Thereafter on the one hand Thrombin-like activity is generated in vitro and on the other hand the thrombin activity decreases in the thrombin-supplemented plasma.

EXAMPLE 11

Stabilization of Samples by Arginine

The samples of example 10 were supplemented with 0–300 mM arginine, pH 8.7, incubated for 17 Stunden at RT, and then the GACA (100 µl sample +50 µl 1.7 mM HD-CHG-Ala-Arg-pNA in 6.4 g/l EDTA, 750 mM arginine, pH 8.7) was performed. Result: Usage of more than 150 mM arginine, preferentially more than 200 mM arginine, particularly ≧250 mM arginine results in stabilization of the sample; the original values (GACA-values before 17 h incubation) can be reproduced even after 17 h at RT.

EXAMPLE 12

Optimization of the Time of Activation in the 2-Step-CPC

The CPC-Test was performed as follows: to 100 µl normal EDTA-plasma 50 µl Pathromtin SL® (SiO$_2$ with phospholipids; DadeBehring) were added. After an activation time of 2 min (RT) 50 µl of the GACA-substrate (here: 1.7 mM HD-CHG-Ala-Arg-pNA in 750 mM arginine, 6.4 g/l EDTA, pH 8.7) were added and the change in extinction/incubation time (in mA/t) was determined.

Result: it appears a linear relationship between invubation time and resulting change in extinction at 405 nm (approx. 35 mA/min). The the activation time of the 2-step-CPC was varied from 0 to 7.5 min (RT). After an incubation time from 0 to 16 min (RT) (RT) the change in extinction at 405 nm was determined. Result: the optimal activation time at RT is 1.5 bis 5 min, preferentially 2 bis 4 min, particularly 2.5–3 min (corresponding to approx. 1 min at 37° C.).

EXAMPLE 13

Standardization of the CPC-Test with a Pure Thrombin-Reagent

The 2-step-CPC was performed as described in example 12, as additional sample a pure thrombin-reagent was used (1000 mIU/ml in 500 mM arginine, 2% Haemaccel®, 0.1% Triton X 100®, pH 8.7). Result: the resulting enzyme activity for the plasma sample in the 2-step-CPC corresponds to 165 mIU/ml thrombin.

EXAMPLE 14

Inhibition of the CPC by Arginine

The CPC-test was performed in the 1-step mode as follows: 100 µl normal plasma, containing increasing concentrations of arginine (0–300 mM), pH 8.7 were incubated with 50 µl 1.7 mM HD-CHG-Ala-Arg-pNA in aqua dest. and 50 µl Pathromtin SLO. The increase in absorbance/t (t=0–10 min RT) was determined. Result: at plasmatic concentrations of arginine above 100 mM the Pathromtin SL®-CPC is decreased to 0% (compared to a normal plasma without arginine=100%).

EXAMPLE 15

Optimization of the Substrate Concentration in the 1-Step-CPC

100 µl normal EDTA-plasma and 100 µl normal EDTA-plasma, supplemented with 120 mIU/ml bovine thrombin, were incubated with 50 µl HD-CHG-Ala-Arg-pNA of increasing conentration (0–1.5 mM final concentration in test) in $H_2O$ und 50 µl Pathromtin SL® for 4 min at RT. The resulting change in extinction was determined by a photometer at 405 nm. Result: the maximal velocity of enzyme is approx. 650 mA/4 min (RT). Halfmaximal velocity occurs at a test concentration of approx. 0.4 mM HD-CHG-Ala-Arg-pNA. In this approach there exists no difference between normal plasma and pathoplasma, such as appearing in example 3 or 6. (s. table 4).

TABLE 4

Optimization of substrate concentration in the 1-step-CPC

| Final Conc. of Substrate [mM] | Enz.-act. Normal Plasma [mA/4 min] | Enz.-act. Pathoplasma [mA/4 min] |
|---|---|---|
| 0 | 0 | 0 |
| 0.14 | 105 | 123 |
| 0.19 | 180 | 173 |
| 0.27 | 232 | 247 |
| 0.38 | 301 | 342 |
| 0.54 | 454 | 428 |
| 0.76 | 607 | 573 |
| 1.07 | 614 | 526 |
| 1.5 | 595 | 570 |

EXAMPLE 16

Reaction Kinetic of the 1-Step-CPC

100 µl Control Plasma N® oder 100 µl 2000 mIU/ml bovine thrombin in 500 mM arginine, 2% Haemaccel®, 0.1% Triton X 100®, pH 8.7, were incubated with 50 µl 1.7 mM HD-CHG-Ala-Arg-pNA in $H_2O$ and 50 µl Pathromtin SL® ($SiO_2$) at RT (1-step-CPC). The resultilng absorbance at 405 nm was determined by a photometer. Result: after 0, 1, 2, 3, 4, 5, 6, 7, 8, 9, 10 min RT the increases in extinction to the 0 min value were: 0, 610, 940, 1076, 1174, 1234, 1292, 1318, 1334, 1356 mA.

EXAMPLE 17

Comparison of Different CPC-Approaches

For n=22 citrated plasmas of patients and the Control Plasma N® (CPN) the following CPC-approaches were performed: 2-step-approaches A, B, C and 1-step-approaches D, E, F.

A) 50 µl Plasma +25 µl Pathromtin SL® ($SiO_2$)

B) 50 µl Plasma +25 µl Pathromtin® (kaolin, in $H_2O$ twofold diluted)

C) 50 µl Plasma +25 µl Neothromtin® (ellagic acid)

3 min RT time of activation; +25 µl 1.7 mM HD-CHG-Ala-Arg-pNA, 750 mM arginine, 6.4 g/l EDTA, pH 8.7

D) 50 µl Plasma +25 µl 1.7 mM $CH_3SO_2$-D-CHG-Gly-Arg-pNA

E) 50 µl Plasma +13 µl 1.5 M arginine, pH 8.7, +50 µl 1.7 mM $CH_3SO_2$-D-CHG-Gly-Arg-pNA F) 50 µl Plasma +25 µl 1.7 mM HD-CHG-Ala-Arg-pNA in $H_2O$+25 µl Pathromtin SL®

Determination of delta A at 405 nm (RT). The respective changes in extinction were correlated with each other. Result: Pathromtin SL®-2-step-CPC correlated with Pathromtin SL®-1-step-CPC with r=0.798 (delta A/13 min (RT) for CPN im 2-step-CPC=354 mA; delta A/2 min (RT) for CPN=547 mA, i.e. in the 1-step-CPC a 10 fach higher Thrombin-Like Activity is generated compared with the 2-step-CPC; the corresponding values for approaches B) and C) are approx. 30% or 20% lower, respectively. Pathromtin-SL®-2-step-CPC correlated with Pathromtin®-2-step-CPC with r=0.506, with Neothromtin®-2-step-CPC with r=0.602 and with $CH_3SO_2$-D-CHG-Gly-Arg-pNA-1-step-CPC with r=0.502. A slightly negative correlation with r=−0.533 resulted for the comparison of Pathromtin SL®-1-step-CPC with $CH_3SO_2$-D-CHG-Gly-Arg-pNA-1-step-CPC. 1-step-CPC with $CH_3SO_2$-D-CHG-Gly-Arg-pNA in presence and absence of arginine (here: 222 mM arginine final, approach D versus approach E) correlated with r=0.768. Thus, even in arginine-stabilized plasma the amidolytic activity against CH$_3$SO$_2$-D-CHG-Gly-Arg-pNA can reliably be determined, what is valid for chromogenic substrates with a CH$_3$SO$_2$-group.

EXAMPLE 18

Increase of Extinction (E) by Increase of Layer Thickness (d; E=εc·d)

The own-extinctions of n=290 citrated plasmas of patients Citratplasmen were determined in a microtiter plate reader (using 100 µl sample volume). Result: the mean own extinction at 405 nm was 210.1 mA, the standard deviation was 72.3 mA. Therefore, using a 4–8 fold layer thickness of the measuring cuvette the necessary reaction time to get an increase in extinction of about 300 mA can be shortened to 25%–12.5%, respectively. This corresponds to an increase in extinction of 300 mA/30–15 min (37° C.), respectively. Using a sensitive photometer, the GACA-activity of a normal plasma is 10–30 mA/min. Plasmas with high own-extinction (>200% of normal) are diluted with 500 mM arginine.

EXAMPLE 19

CV-values for GACA and CPC

GACA (100 µl sample+50 µl HD-CHG-Ala-Arg-pNA, 6.4 g/l EDTA, 750 mM arginine, pH 8.7) and CPC (100 µl sample+50 µl 1.7 mM HD-CHG-Ala-Arg-pNA, 6.4 g/l EDTA+50 µl Pathromtin SL®) were performed with Control Plasma N®, STA Preciclot I®, STA Preciclot II® and with pooled patient plasmas in 10fach-determination. Result: the intra-assay-coefficients of variation (CV) values for GACA and CPC are between 1% and 4%.

EXAMPLE 20

Detection of Active Trypsin in Plasma

25 µl plasma of a pancreatitis-patient (citrated), 25 pi CPN, 25 µl 36 pkat/ml bovine Factor Xa in PBS, 0.1% Triton X 100®, were incubated with 25 µl assay buffer, containing 600 mM NaHCO$_3$, pH 8.7 with and without 600 mM arginine, 25 µl 25 mM chloramine T®, 25 µl 3 mM N-α-Z-D-Arg-Gly-Arg-pNA.2HCl (S-2765®; Chromogenix, Molndal, Schweden) and 25 µl Aprotinin (0, 2, 20, 200, 2000, 20000 KlU/ml) for 50 min at 37° C. and the increase in extinction at 405 nm during this incubation time was determined wiwth a microtiterplate-photometer.

Result: Usage of 25 µl 0, 2, 20, 200, 2000, 20000 KlU/ml resulted in presence of arginine in increases of extinction of 788, 778, 709, 685, 497, 259 mA, respectively, and in absence of arginine in increases of extinction of 738, 733, 715, 531, 294, 103 mA, respectively. The respective increases in extinction in the CPN were 131, 133, 126, 126, 125, 123 mA in presence of arginine and 122, 134, 135, 108, 118, 124 mA in the absence of arginine. Pure factor Xa—in contrast to active trypsin (as other active serine proteases interacting with α2-macroglobulin) is not inhibited by aprotinin. With the assay system according to the invention active trypsin in blood can be detected, a marker for the presence and/or the severity of pancreatitis.

List of Abbreviations

| | |
|---|---|
| A | Absorbance units |
| Abu | L-alpha-Aminobutyric acid |
| Ala | Alanine |
| APTT | activated partial thromboplastin time |
| Arg | Arginine |
| But | Butyl |
| Bz | Benzoyl |
| CHA | β-Cyclohexylalanine |
| CH$_3$CO | Acetyl |
| CH$_3$OCO | Methoxycarbonyl |
| CH$_3$SO$_2$ | methane sulfonyl |
| CHG | Cyclohexylglycine |
| CP | Control Plasma N ® |
| CPC | Contact Phase Capacity |
| CV | Coefficient of Variation |
| d | Layer thickness |
| DIC | Disseminated Intravascular Coagulation |
| E | Extinction |
| EDTA | Ethylene Diamine Tetraacetic acid |
| EGTA | Ethylene Glycol-bis(β-aminoethyl Ether)N,N,N',N'-Tetraacetic Acid |
| Enz.-act. | Enzyme activity |
| F IIa | Factor IIa, Thrombin |
| Fbgen | Fibrinogen |
| FEIBA | Factor-Eight-Inhibitor-Bypassing-Activity |
| GACA | Global Assay of in-vivo Coagulation Activation |
| Glu | Glutamic acid |
| Gly | Glycine |
| HHT | Cyclohexyltyrosine |
| Ile | Isoleucine |
| KIU | Kallikrein Inhibiting Units |
| K$_m$ | Michaelis-Constant |
| Leu | Leucine |
| Lys | Lysine |
| mA | milli absorbance units |
| mIU | milli international units |
| mM | mmol/l |
| PBS | Phosphate Buffered Saline |
| Phe | Phenylalanine |
| Pip | Pipecolic acid |
| Pro | Proline |
| PT | Prothrombin Time |
| pNA | para-Nitroanilide |
| Suc | Succinyl |
| t | time |
| TT | Thrombin Time |
| uGACA | uncorrected GACA |
| Val | Valine |

What is claimed is:

1. A method for the determination of the in vivo activity of a hemostasis protease in a biological fluid supplemented with arginine and/or guanidine comprising the steps of incubating a first sample of the biological fluid with at least one chromogenic or fluorogenic substrate for the hemostasis protease, the chromogenic or fluorogenic substrate present at a final test concentration in the first sample, and detecting chromogenic or fluorogenic activity, wherein hemostasis proteases are not artificially activated prior to detection.

2. A method according to claim 1, whereby the biological fluid is selected from the group consisting of a cell culture, a compartment fluid, blood and plasma.

3. A method according to claim 2, wherein the supplemented blood or plasma is EDTA/arginine-blood, EDTA/arginine-plasma, EDTA/guanidine-blood, EDTA/guanidine-plasma, arginine/N-chloro-p-toluene-blood or arginine/N-chloro-p-toluene-plasma.

4. A method according to claim 1, whereby the chromogenic or fluorogenic substrate is used in a final test concentration of 0.05 to 1 mM, and/or in an amount of up to 3 nmoles/µl sample.

5. A method according to claim 1 wherein the hemostasis protease is involved in the contact phase of hemostasis in biological fluids, further comprising the additional steps of incubating a second sample of the biological fluid with the chromogenic or fluorogenic substrate in the presence of at least one contact phase activator, detecting chromogenic or fluorogenic activity in the second sample, comparing the chromogenic or fluorogenic activity of the two samples and determining a corrected activation of coagulation measurement.

6. A method according to claim 5, whereby the chromogenic or fluorogenic substrate is a methoxysulfonated or acetylated substrate for a hemostasis enzyme.

7. A method according to claim 6, whereby the methoxysulfonated or acetylated substrate for a hemostasis enzyme is selected from the group consisting of Pefa IXa ($CH_3SO_2$-D-CHG-Gly-Arg-pNA), Pefa VIIa ($CH_3SO_2$-D-CHA-But-Arg-pNA) and Pefa Xa ($CH_3OCO$-D-CHA-Gly-Arg-pNA).

8. A method according to claim 5, whereby the biological fluid is selected from the group consisting of a cell culture, a compartment fluid, blood and plasma.

9. A method according to claim 8, wherein the supplemented blood or plasma is EDTA/arginine-blood, EDTA/arginine-plasma, EDTA/guanidine-blood, EDTA/guanidine-plasma, arginine/N-chloro-p-toluene-blood or arginine/N-chloro-p-toluene-plasma.

10. A method according to claim 6, whereby the chromogenic or fluorogenic substrate is used in a final test concentration of 0.05 to 1 mM.

11. A method to determine the in vivo activity of trypsin and/or subtilisin in a biological fluid supplemented with arginine and/or guanidine, comprising incubating the biological fluid with at least one chromogenic or fluorogenic substrate for trypsin and/or for subtilisin and detecting chromogenic or fluorogenic activity, wherein trypsin and/or subtilisin are not artificially activated prior to detection.

12. A method according to claim 11, whereby the biological fluid is selected from the group consisting of a cell culture, a compartment fluid, blood and plasma.

13. A method according to claim 12, wherein the supplemented blood or plasma is EDTA/arginine-blood, EDTA/arginine-plasma, EDTA/guanidine-blood, EDTA/guanidine-plasma, arginine/N-chloro-p-toluene-blood or arginine/N-chloro-p-toluene-plasma.

14. A method according to claim 11, whereby the chromogenic or fluorogenic substrate is used in a concentration of up to 1 mM.

15. A method for the diagnosis of the in vivo activity of hemostasis of a biological fluid, said method comprising determining the in vivo activity of a hemostasis protease according to claim 1 and using the detection results to diagnose a hemostatic disorder.

16. A method for the diagnosis of septicemia or of pancreatitis or of the degree of severity of pancreatitis, said method comprising determining the in vivo activity of trypsin and/or subtilisin in a biological fluid according to claim 11 and using the detection results to diagnose septicemia or pancreatitis or the severity of pancreatitis.

17. A method according to claim 4, whereby the chromogenic or fluorogenic substrate is used in a final test concentration of 0.5 to 0.6 mM and/or in an amount of up to 1.5 nmoles/µl sample.

18. A method according to claim 10, whereby the chromogenic or fluorogenic substrate is used in a final test concentration of 0.4 to 0.6 mM.

19. A method according to claim 14, whereby the chromogenic or fluorogenic substrate is used in a final test concentration of 0.3 to 0.6 mM.

* * * * *